US012714381B2

(12) United States Patent
Benassi et al.

(10) Patent No.: US 12,714,381 B2
(45) Date of Patent: Aug. 25, 2026

(54) MEDICAL APPARATUS FOR X-RAY ANALYSIS HAVING MOVABLE SUPPORT FOR BREAST

(71) Applicant: IMS GIOTTO S.P.A., Sasso Marconi (IT)

(72) Inventors: Matteo Benassi, Casalecchio di Reno (IT); Massimo Morselli, San Felice sul Panaro (IT); Alessandro Turco, Vado di Monzuno (IT); Paolo Vignoli, San Giovanni in Persiceto (IT)

(73) Assignee: IMS GIOTTO S.P.A., Sasso Marconi (IT)

( * ) Notice: Subject to any disclaimer, the term of this patent is extended or adjusted under 35 U.S.C. 154(b) by 321 days.

(21) Appl. No.: 18/167,258

(22) Filed: Feb. 10, 2023

(65) Prior Publication Data

US 2023/0255580 A1 Aug. 17, 2023

(30) Foreign Application Priority Data

Feb. 14, 2022 (IT) ........................ 102022000002660

(51) Int. Cl.
*A61B 6/50* (2024.01)
*A61B 6/00* (2024.01)
(Continued)

(52) U.S. Cl.
CPC .............. *A61B 6/502* (2013.01); *A61B 6/022* (2013.01); *A61B 6/0414* (2013.01); *A61B 6/102* (2013.01);
(Continued)

(58) Field of Classification Search
CPC ......... A61B 5/708; A61B 6/502; A61B 6/022; A61B 6/0414; A61B 6/102; A61B 6/12;
(Continued)

(56) References Cited

U.S. PATENT DOCUMENTS 5,553,111 A * 9/1996 Moore .................. A61B 6/502 378/208
6,845,146 B2 * 1/2005 Rick ..................... A61B 6/502 378/37

(Continued)

FOREIGN PATENT DOCUMENTS

EP 2517627 B1 8/2015
EP 3023076 A1 5/2016

(Continued)

OTHER PUBLICATIONS

Italian Search Report dated Sep. 29, 2022 from counterpart Italian Patent Application No. 2022000002660.

*Primary Examiner* — Anne M Kozak
*Assistant Examiner* — Jason P Gross
(74) *Attorney, Agent, or Firm* — SHUTTLEWORTH & INGERSOLL, PLC; Timothy J. Klima

(57) ABSTRACT

A medical apparatus for X-ray analysis, includes a source for X-rays, a detector defining a detection plane, a probe with a needle for treating the patient, an immobiliser, a frame supporting the source, the detector, the immobiliser and the probe. A control unit connects to the source and detector. The probe is connected to the frame movably along a first direction, a second direction perpendicular to the first direction and a third direction at right angles to the detection plane, the first direction and the second direction lying in a plane parallel to the detection plane. The apparatus moves the probe in a zone above the immobiliser and positions the needle, along the first direction, in the zone and in the right and left side relative to the immobiliser. The immobiliser is connected to the frame and is movable, independently of the probe, along the third direction.

25 Claims, 14 Drawing Sheets

(51) Int. Cl.
*A61B 6/02* (2006.01)
*A61B 6/04* (2006.01)
*A61B 6/10* (2006.01)
*A61B 6/12* (2006.01)
*A61B 10/00* (2006.01)
*A61B 10/02* (2006.01)

(52) U.S. Cl.
CPC .............. *A61B 6/12* (2013.01); *A61B 6/4423* (2013.01); *A61B 6/547* (2013.01); *A61B 6/0435* (2013.01); *A61B 10/0041* (2013.01); *A61B 10/0233* (2013.01)

(58) Field of Classification Search
CPC ..... A61B 6/4423; A61B 6/547; A61B 6/0435; A61B 10/0041; A61B 10/0233; A61B 10/02; A61B 17/3403; A61B 2017/3407; A61B 2017/3411; A61B 90/17
See application file for complete search history.

(56) References Cited

U.S. PATENT DOCUMENTS 7,110,614 B2 * 9/2006 Launay .................. G06T 7/579 382/280
7,869,563 B2 * 1/2011 Defreitas .............. A61B 6/107 378/114
10,772,584 B2 * 9/2020 Defreitas ................ A61B 6/04
2007/0016067 A1 * 1/2007 Webster, III .......... A61B 90/10 600/464
2008/0080673 A1 * 4/2008 Yamakita ............ A61B 6/0414 378/155
2010/0046698 A1 * 2/2010 Lebovic ................ A61B 6/502 378/37
2010/0113970 A1 * 5/2010 Okada ............... A61B 10/0266 600/562
2011/0087132 A1 4/2011 Defreitas et al.
2011/0118625 A1 * 5/2011 Akuzawa .............. A61B 90/11 600/567
2012/0053455 A1 3/2012 Okada
2012/0143029 A1 * 6/2012 Silverstein .......... A61B 8/0891 600/374
2013/0129039 A1 * 5/2013 DeFreitas ............. A61B 6/502 378/208
2016/0113599 A1 * 4/2016 Albanese .............. A61B 6/469 600/424
2016/0183898 A1 6/2016 Cormican et al.
2016/0310215 A1 * 10/2016 Palma ................... A61B 34/10
2017/0340303 A1 * 11/2017 Stango .................. A61B 90/17
2018/0035984 A1 2/2018 Schmitt et al.
2019/0130563 A1 * 5/2019 Vecchio ................ A61B 6/502
2019/0209106 A1 7/2019 Bechtold et al.
2020/0359974 A1 * 11/2020 Defreitas .............. A61B 6/502
2021/0030375 A1 * 2/2021 Defreitas ............ A61B 6/0414
2022/0192614 A1 * 6/2022 Vancamberg ........ A61B 6/4458
2022/0233165 A1 * 7/2022 Park .................... A61B 6/5247
2022/0370052 A1 * 11/2022 DeFreitas .......... A61B 10/0275

FOREIGN PATENT DOCUMENTS

EP 3120773 A1 1/2017
EP 3476297 A1 5/2019

* cited by examiner 1
2
3
6
16
16
56
10
11
4
50
S
55
52
51
15
7
Z
X
Y 1
2
3
6
16
16
56
50
55
52
10
11
S
15
7
4
Z
X
Y 1
2
3
6
16
16
A2
56
A3
30
50
55
12
11
31
10
13
5
S
14
7
15
4
Z
X
Y 1
2
3
6
16
16
56
50
55
12
11
A1
70
S
5
51
14
7
4
Z
X
Y 1
2
3
6
103
A2
110
A1
16
101
102
107
111
51
104
109
A3
11
108
105
106
14
7
S
4
Z
X
Y 1
2
3
6
16
16
50
51
54
12
11
10
13
14
15
7
S
4
Z
X
Y 1
2
3
6
103
16
56
16
50
104
51
11
14
S
7
15
4
Z
X
Y 1
2
3
6
16
16
50
12
11
7
51
56
A1
S
4
Z
X
Y 1
2
3
6
16
16
A2
55
56
50
52
51
11
A1
S
5
54
4
7
14
Z
X
Y 1
2
3
6
16
16
20
A2
57A
58A,58B
57B
9
53
U
32
52
54
51
A1
Z
X
Y 1
2
3
6
16
16
56
55
50
8
11
4
S
15
8
Z
X
Y

MEDICAL APPARATUS FOR X-RAY ANALYSIS HAVING MOVABLE SUPPORT FOR BREAST

This application claims priority to Italian Patent Application 102022000002660 filed Feb. 14, 2022, the entirety of which is incorporated by reference herein.

This invention relates to a medical apparatus for X-ray analyses.

There are known medical X-ray apparatuses which comprise a source configured to emit X-rays and a detector configured to receive the X-rays emitted by the source.

These apparatuses are also equipped with a biopsy probe, which is provided with a needle to allow a sample to be taken of a portion of tissue from the patient's breast for subsequent analyses.

In order to perform the above-mentioned medical analyses, in particular the biopsy, the patient's breast is interposed between the X-ray source and the detector, and the breast is compressed using an immobilising device.

In these circumstances, the probe is moved close to the breast so that a tissue sample can be taken by the needle can be taken in a zone of interest.

A strongly felt need in the sector in question is that of having a machine which is particularly flexible and versatile, in particular regarding the possibilities of approach of the needle with respect to the patient. In effect, the position of the patient's breast is generally determined by the position of the source and of the detector; under these circumstances, in prior art machines, the medical staff often complain of the difficulty of positioning the needle and this may increase the positioning time, as well as the need to reposition the patient's breast or, alternatively, having to mount the probe in different positions where this is possible. Whatever the case, as mentioned, in the prior art machines the patient's breast must be repositioned or parts of the machine must be disassembled/fitted in different positions.

An aim of the invention is to satisfy the requirement expressed in the introduction, that is to say, to provide an apparatus and a method for X-ray examinations which can perform the biopsy in a particularly flexible and versatile way, in particular with regard to the possibility of approaching the patient's breast with the needle according to a plurality of directions.

The features of the invention are clearly described in the claims below and its advantages are more apparent from the detailed description which follows, with reference to the accompanying drawings which illustrate a preferred, non-limiting example embodiment of the invention and in which:

Figure 1A:
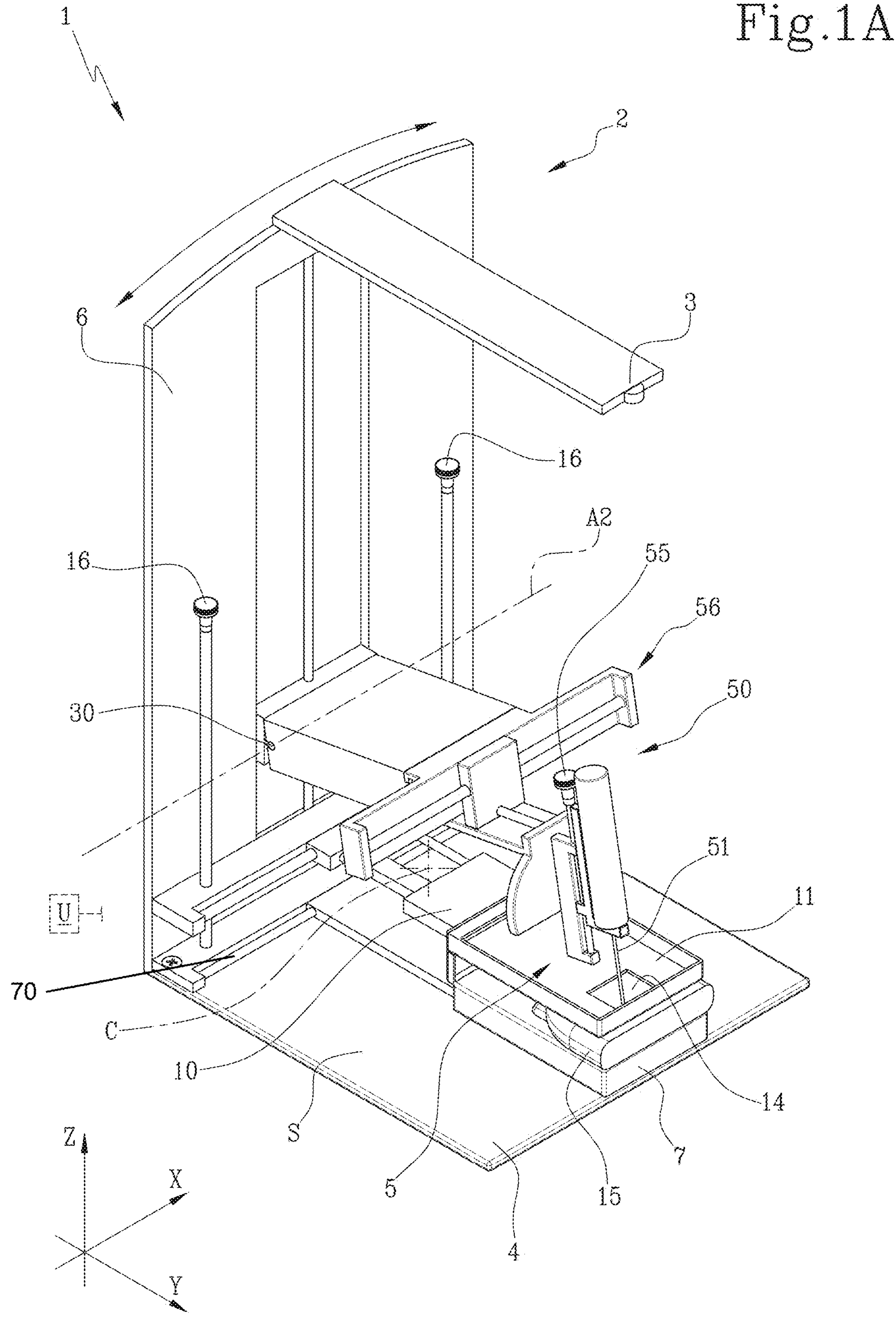
FIGS. 1A, 1B and 1C are perspective views of three different operating configurations of an embodiment of the apparatus according to the invention.

It should be noted that all the drawings are schematic and are therefore not representative of the actual dimensions of the system.

The numeral 1 denotes a medical apparatus for X-ray analysis.

The apparatus 1 can allow a biopsy examination to be performed.

The apparatus 1 comprises a machine 2 for allowing a diagnosis, equipped with:

at least one source 3 configured to emit X-rays, at least one X-ray detector 4 defining a detection plane S;

a probe 50 equipped with a needle 51 for the treatment of the body of a patient;

an immobiliser 10 comprising an immobilising element 11;

a supporting frame 6, supporting the at least one source 3, the at least one X-ray detector 4, the immobiliser 10 and the probe 50;

a control unit U connected at least to the source 3 and to the X-ray detector 4.

According to the invention, the probe 50 is connected to the supporting frame 6 movably along a first axis X, along a second direction Y perpendicular to the first direction X and along a third direction Z at right angles to the detection plane S, the first direction X and the second direction Y lying in a plane parallel to the detection plane S, the apparatus 1 is configured for moving said probe 50 in the zone 5 above the immobiliser 10 and allow a positioning of the needle 51, along the first direction X, selectively in the zone 5 above the immobiliser 10 and in the right and left side relative to the immobiliser 10. According to an aspect of the invention, the apparatus 1 comprises a first actuator 101 configured to move the probe 50 along the first direction X.

According to an aspect of the invention, the apparatus 1 comprises a second actuator 102 configured to move the probe 50 along the second direction Y.

According to an aspect of the invention, the apparatus 1 comprises a third actuator 103 configured to move the probe 50 along the third direction Z.

According to another aspect, the immobiliser 10 is connected to the supporting frame 6 and is movable, independently of the probe 50, at least along the third direction Z.

According to an aspect of the invention, the apparatus 1 comprises a fourth actuator 104 configured to move the immobiliser 10 along the third direction Z.

According to an aspect of the invention, the immobiliser 10 is configured to allow a movement along the third direction Z for a stroke of between 10 mm and 200 mm, more preferably between 50 mm and 120 mm, even more preferably for a stroke of between 70 mm and 90 mm.

According to an aspect of the invention, the apparatus 1 comprises at least one knob 16 for locking the immobiliser 10. The locking knob 16 is designed to lock the movement of the immobiliser 10 along the third direction Z.

The immobiliser 10 is configured to immobilise a breast 15 of a patient.

According to an aspect, the immobiliser 10 is configured to compress the breast 15.

The breast 15 is illustrated schematically in the accompanying drawings.

Advantageously, once the immobiliser 10 has been positioned in contact with the breast 15 in order to immobilise it and compress it, the blocking of movement of the immobiliser 10 along the third direction Z by means of the locking knob 16 prevents movements of the immobiliser 10 which could cause pain for the patient or errors during the examination procedures. In fact, a sudden movement of the immobiliser 10 towards the breast 15 would cause excessive compression and hence possible pain for the patient. Vice versa, an unexpected movement in the opposite direction would result in the breast 15 not being correctly immobilised and compressed during an analysis procedure.

Advantageously, the apparatus 1 according to the invention is particularly compact and allows a biopsy examination to be performed without repositioning the breast 15 of the patient immobilised using the immobiliser 10. In effect, the probe 50 may be moved, selectively, that is to say, by means of a setting or action by the user, to the right or to the left relative to the immobiliser 10.

The probe 50, in its movement between the right and left parts of the immobiliser 10, passes through the region above the immobiliser 10.

It should also be noted that the probe 50 may also be positioned in the region above the immobiliser 10.

This facilitates examination of the patient both with regard to the positioning of the breast 15 and with regard to the operations to be performed by the dedicated medical staff.

According to an aspect of the invention, the probe 50 is configured to allow a movement along the first direction X for a stroke of between 50 mm and 400 mm, more preferably between 60 mm and 200 mm, even more preferably for a stroke of between 80 mm and 120 mm.

It should be noted that the above-mentioned positioning to the right or to the left of the probe 50 relative to the immobiliser 10 is to be considered along the first direction X.

According to an aspect of the invention, the probe 50 is configured to allow a movement along the second direction Y for a stroke of between 50 mm and 300 mm, more preferably between 60 mm and 200 mm, even more preferably for a stroke of between 80 mm and 120 mm.

According to an aspect of the invention, the probe 50 is configured to allow a movement along the third direction Z for a stroke of between 150 mm and 350 mm, more preferably between 200 mm and 300 mm, even more preferably for a stroke of between 240 mm and 280 mm.

According to another aspect, said probe 50 is a biopsy probe.

It should also be noted that the immobiliser 10 has an upper opening 14, through which the needle 51 can pass to perform a biopsy examination.

The opening 14 is preferably square in shape.

Preferably, the side of this opening is between 30 mm and 70 mm; still more preferably, between 40 mm and 60 mm.

The immobilising element 11 of the immobiliser 10 extends along the first direction X between 80 mm and 200 mm and extends along the second direction Y between 80 mm and 250 mm.

It should be noted that the immobiliser 10 is movable, preferably continuously, independently of the probe 50, along the first direction X.

According to an aspect of the invention, the immobiliser 10 is configured to allow a movement along the first direction X for a stroke of between 50 mm and 120 mm, more preferably between 60 mm and 100 mm, even more preferably for a stroke of between 70 mm and 90 mm.

According to an aspect of the invention, the apparatus 1 comprises a fifth actuator 105 configured to move the immobiliser 10 along the first direction X.

According to another aspect, the immobiliser 10 is movable, preferably continuously, independently of the probe 50, along the second direction Y.

According to an aspect of the invention, the immobiliser 10 is configured to allow a movement along the second direction Y for a stroke of between 50 mm and 120 mm, more preferably between 60 mm and 100 mm, even more preferably for a stroke of between 70 mm and 90 mm.

According to an aspect of the invention, the apparatus 1 comprises a sixth actuator 106 configured to move the immobiliser 10 along the second direction Y.

It should also be noted that the probe 50 is movable in rotation about a first axis of rotation A1. The first axis A1 is angularly positioned relative to the third direction Z, that is to say, angularly positioned relative to a direction perpendicular to the detection plane S, preferably by an angle of between 0° and 10°, more preferably between 4° and 8°.

According to an aspect of the invention, the probe 50 is configured to allow the rotation about the first axis of rotation A1 of between 0° and 250°, considering that the configurations wherein the probe 50 is positioned with the needle 51 parallel to the detection plane S to the left and to the right of the immobiliser 10 relative to the first direction X correspond, respectively, to an angle of 35° and 215°.

According to an aspect of the invention, the apparatus 1 comprises a seventh actuator 107 configured to move the probe 50 in rotation about the first axis of rotation A1.

Advantageously, the rotation of the probe 50 about the first axis of rotation A1, together with the movements of the probe 50 itself along the first direction X, the second direction Y and the third direction Z, allows the needle 51 of the probe 50 to approach the breast 15 from different operating positions.

According to another aspect, the machine 2 comprises a member 7 for supporting the breast 15, removably connected to the supporting frame 6 and positioned between the detection plane S and the immobiliser 10.

The member 7 for supporting the breast 15 being rigid and movable along the first direction X along a support guide 70 aligned along the first direction X.

According to an aspect, the member 7 for supporting the breast 15 is movable along the first direction X independently, preferably continuously, with respect to the immobiliser 10.

According to an aspect of the invention, the member 7 for supporting the breast 15 is configured to allow a movement along the first direction X for a stroke of between 50 mm and 120 mm, more preferably between 60 mm and 100 mm, even more preferably for a stroke of between 70 mm and 90 mm.

According to an aspect of the invention, the apparatus 1 comprises an eighth actuator 108 configured to move the member 7 for supporting the breast 15 along the first direction X.

According to an aspect, the machine 2 comprises a system 8 for covering the detector 4 and/or the member 7 for supporting the breast 15, removably couplable to the detector 4 and/or to the member 7 for supporting the breast 15.

The covering system 8 comprises a casing, which may be positioned above the detector 4, to be replaced for each examination; this guarantees the safety of the machine 2 from the hygiene and medical points of view.

According to another aspect, the covering system 8 comprises a casing which may be positioned above the member 7 for supporting the breast 15.

More generally speaking, it should be noted that the casing of the covering system 8 may enclose one or both of the detector 4 and the supporting member 7.

Preferably, the casing is made of plastic material (and is of the disposable type, that is to say, it can be replaced after each use of the machine).

The system 8 for covering the detector 4 and/or the member 7 for supporting the breast 15 is disposable or sterilisable.

According to another aspect, the machine 2 comprises at least one sensor 9 connected to the control unit U and configured to detect impacts of the probe 50 in the movement of the probe, along the third direction Z and/or along the first direction X and/or the second direction Y.

In this way, advantageously, it is possible to check whether during the examination there have been impacts by the probe 50: this makes it possible to detect unexpected collisions with machine elements or parts of the human body of the patient or of the operator.

Preferably, the sensor 9 is a force sensor; more preferably a sensor of the load cell type.

According to an aspect, the probe 50 comprises a needle 51 and a device 52 for supporting the needle 51.

According to an aspect of the invention, the supporting device 52 of the needle 51 is configured to allow a translation for a stroke of between 140 mm and 220 mm, preferably between 160 mm and 200 mm.

In other words, the supporting device 52 of the needle 51 is configured for a movement which allows the needle 51, in use, to advance or to withdraw relative to the biopsy sampling zone and therefore relative to the breast 15.

According to an aspect of the invention, the apparatus 1 comprises a ninth actuator 109 configured to move the supporting device 52 of the needle 51 towards and away, in use, from the breast 15.

According to one aspect, the apparatus 1 comprises a control knob 55 configured to translate the supporting device 52 of the needle 51 to allow the needle 51, in use, to move forward or to withdraw relative to the biopsy sampling zone and therefore relative to the breast 15.

The control knob 55 allows the supporting device 52 of the needle 51 to be moved manually and/or to lock it, again manually, in a predetermined position.

The apparatus 1 comprises a distance sensor 53 connected to the control unit U and configured to measure the distance between the tip of the needle 51 and an end of the supporting device 52 of the needle 51.

Advantageously, according to this aspect, it is possible to check the length of the needle 51, so as to check whether the machine settings are correct for the needle 51 in use.

The distance sensor 53 may be of any type, for example of the optical type or of the potentiometric strips type.

The control unit U is configured to emit a signal if the length measured by the distance sensor 53 of said needle 51 does not correspond to a preset length of a needle.

In that sense, the machine 2 comprises an interface configured to allow selection of a parameter relating to the length of the needle 51 in use.

According to another aspect, the probe 50 comprises a needle holder guide 54 and the distance sensor 53 is positioned on the needle holder guide 54.

According to another aspect, the control unit U is configured to provide a method for identifying the position of the immobiliser 10 and/or a physical characteristic of the breast 15 of the patient, wherein it activates the X-ray source 3 and identifies the position of the immobiliser 10 by analysing the signal received from the detector 4.

In short, when a method for identifying the position of the immobiliser 10 and/or a physical characteristic of the patient's breast 15 is set, it is possible to establish the position of the immobiliser 10 by means of an X-ray analysis. This is particularly useful, since it is possible, by means of an analysis performed in the machine, without providing an additional dose of radiation to the patient, to acquire the positioning of the immobiliser 10 with respect to the breast 15, so as to be able to derive indications of movement of the probe 50 for the biopsy sample.

Moreover, in this manner, it is also possible to detect a physical characteristic of the patient's breast 15 for various purposes, for example to check its position with respect to the immobiliser 10 itself.

The physical characteristic of the patient's breast 15 means, by way of a non-limiting example, the shape, volume, colour, edge, etc.

According to an aspect of the invention, the apparatus 1 is configured for moving the X-ray source 3 along an arc in different positions for acquiring stereotaxic and tomographic images.

The arc has a centre C with a position between the source 3 and the X-ray detector 4.

Preferably, the distance between the centre C of the arc and the detector 4 is less than the distance between the centre C of the arc and the source 3.

Preferably, the distance between the centre C of the arc and the detector 4 is less than or equal to 150 mm, even more preferably less than or equal to 100 mm.

Advantageously, the possibility of positioning the X-ray source 3 in different positions along the arc makes it possible to acquire stereotaxic or tomographic images of the breast 15 and/or of the immobiliser.

Advantageously, the images allow a position of the immobiliser 10 and/or of the breast 15 and/or any lesions of the breast 15 itself to be identified.

Advantageously, these stereotaxic or tomographic images can be acquired during the biopsy procedure, in order mainly to guide the probe 50 during the biopsy examination, or before the procedure, for example to set up an operating plane for moving the probe 50.

Advantageously, the stereotaxic or tomographic images allow reliable information to be obtained even deep inside the breast 15.

According to an aspect, according to these images, the control unit U is configured to move the probe 50 along the first direction X, the second direction Y and the third direction Z.

In fact, it should be noted that when the needle 51 is inserted into the breast 15, the tissues of the breast 15, including any lesion, can move. For this reason, a modification of the path of the needle 51 may be required for the biopsy sampling. The stereotaxic or tomographic images allow the detection of any modification in the position of the tissues and the control unit U is configured to consequently move the probe 50, and therefore the needle 51.

According to another aspect, the machine 2 comprising a viewing system 20 configured to capture images of the immobiliser 10 and/or of the probe 50 and/or of the member 7 for supporting the breast 15 and/or of the breast 15, to identify the position or the physical characteristics of one or more of said immobiliser 10, probe 50, member 7 for supporting the breast 15, relative to a predetermined reference system.

Advantageously, in this way, it is possible to obtain information useful for operation of the machine, through the viewing system 20 itself, in particular with regard to the position of some elements of the machine 2 or of the breast 15 of the patient.

Preferably, the viewing system 20 comprises one or more video cameras, preferably of the stereo type.

The viewing system 20 may also perform the function of anti-collision checking, since the control unit U may be configured to allow a check of the relative positioning of the various components of the machine to identify any abnormal positions which can correspond to a collision condition.

Generally speaking, it should be noted that the information regarding the positions of the breast 15 and/or lesions in the breast 15 and/or components of the machine 2 makes it possible to use all the possible configurations of the apparatus 1 described in this invention in order to optimise the biopsy sampling procedure. In particular, among the other advantages, the optimisation of the configuration of the apparatus 1 allows the sampling path followed by the probe 50 to be minimised and a cut to be made on the breast 15 as small as possible.

According to another aspect, the probe 50 comprises at least one control handle 55 configured to move the probe 50 along the third direction Z.

According to another aspect, the probe 50 comprises a movement system 56 with guides (57A, 57B) and slides (58A, 58B).

The slides (58A, 58B) are movable along said guides (57A, 57B) for movement of the probe 50 along the first direction X and the second direction Y.

According to another aspect, the movement system 56 with guides 57A, 57B and slides 58A, 58B comprises a first guide 57A and a first slide 58A, movable along said first guide 57A, for the movement along the first direction X.

According to another aspect, the movement system 56 with guides (57A, 57B) and slides (58A, 58B) comprises a second guide 57B and a second slide 58B, movable along said second guide 57B, for the movement along the second direction Y.

According to yet another aspect, the immobiliser 10 comprises at least a first tray 12, designed for collecting fluids or organic materials.

Advantageously, in this way, it is possible to collect any bodily fluids (e.g. blood) which may come out during the biopsy operation on the breast 15 of the patient: this increases the hygiene-medical safety of the machine 2.

According to another aspect, the immobiliser 10 comprises at least a second tray 13, designed to collect fluids or organic materials, said second tray 13 being associated with the immobilising element 11.

Preferably, the second tray 13 is made of a deformable material, for example silicone; in this way, it can advantageously be flattened by the immobilising element 11 and/or by the member 7 for supporting the breast 15.

Preferably, the second tray 13 is made of silicone.

The second tray 13 is particularly useful in the case of a biopsy performed laterally with the needle 51: in this case, the fluids are collected by the second tray 13.

It should also be noted that the immobilising element 11 may be replaced from one patient to another, also allowing the replacement of the first and second trays 12, 13: this increases the hygiene-medical safety of the machine itself.

According to another aspect, the probe 50 is connected to the supporting frame 6 by a first hinge 30, so as to rotate according to a second axis A2 parallel to the detection plane S.

The second axis A2 is parallel to the first direction X.

According to an aspect, the rotation of the probe 50 about the second axis A2 is between −15° and 15°, even more preferably between −10° and 10°.

Figure 2:
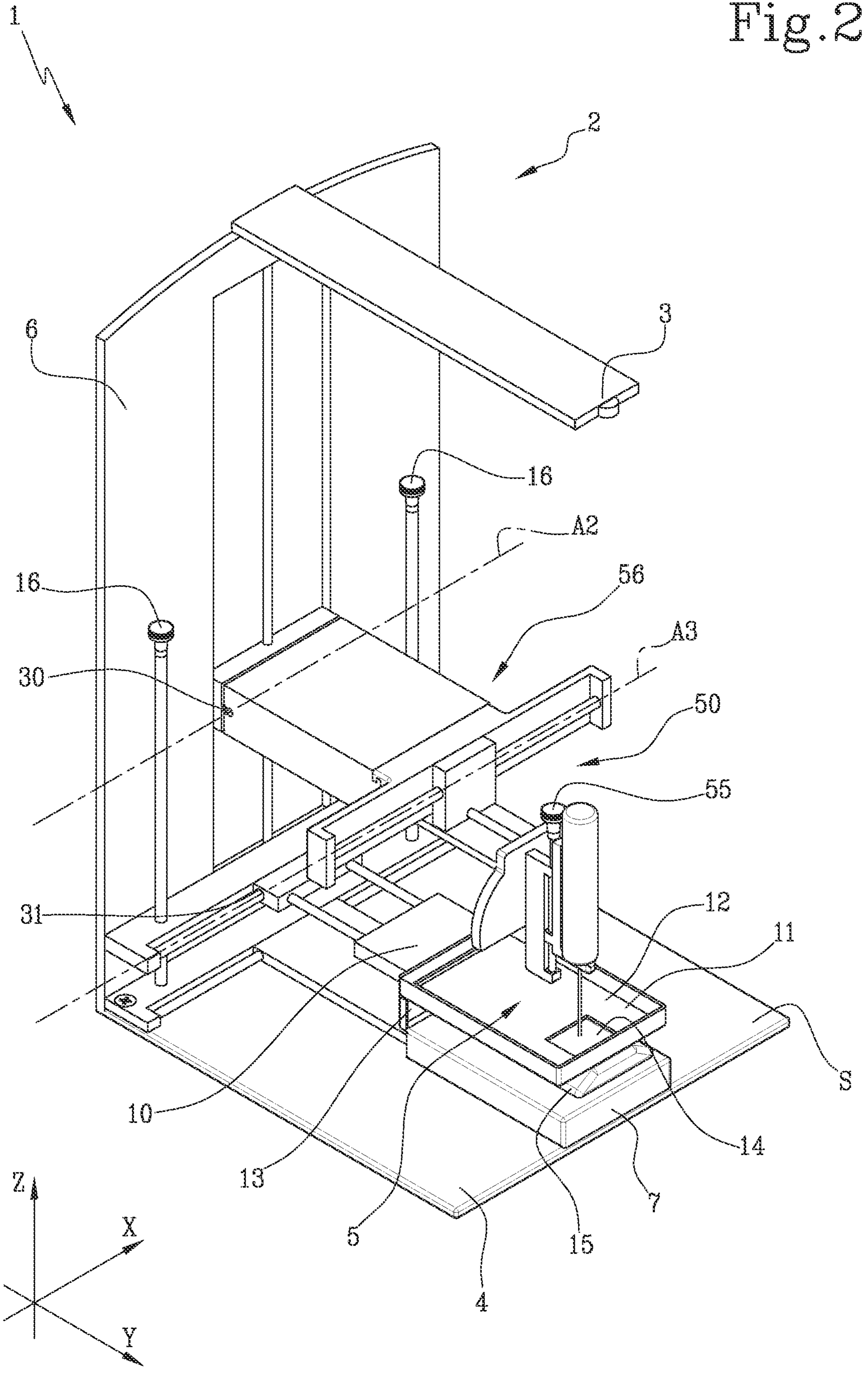
FIGS. 2 to 12 illustrate the apparatus of FIGS. 1A, 1B and 1C in different configurations, that is, with some elements located in different positions.

The angle of rotation 0° of the probe 50 is illustrated in FIG. 2. In FIG. 2, the needle 51 of the probe 50 lies on a plane at a right angle to the detection plane S.

According to an aspect of the invention, the apparatus 1 comprises a tenth actuator 110 configured to move the probe 50 in rotation about the second axis of rotation A2.

According to an embodiment not illustrated in the accompanying drawings, the first hinge 30 is positioned in a zone of the movement system 56 with guides 57A, 57B and slides 58A, 58B close to the slides 58A, 58B.

According to another aspect, the immobiliser 10 is connected to the supporting frame 6 by a second hinge 31, so as to rotate according to a third axis A3 parallel to the detection plane S.

The third axis A3 is parallel to the first direction X.

According to an aspect, considering an angle of 0° when a lower surface of the immobiliser 10 is parallel to the detector 4 (as illustrated for example in FIG. 1A), the rotation of the immobiliser 10 about the third axis A3 is between −15° and 15°, even more preferably between −10° and 10°.

According to an aspect of the invention, the apparatus 1 comprises an eleven actuator 111 configured to move the immobiliser 10 in rotation about the third axis of rotation A3.

Advantageously, the immobiliser 10 can therefore be inclined at various angles towards the breast 15, in such a way as to adapt to each morphology of it. In particular, in this way, the machine 2 is able to adapt in an optimum manner also to small and/or dense breasts 15.

According to an aspect of the invention, the apparatus 1 comprises a further sensor 32, preferably a force sensor, more preferably a sensor of the load cell type, configured to detect the pressure of the immobiliser 10 on the breast 15 and/or any impacts of the immobiliser 10.

The further sensor 32 is configured for communicating with the control unit U.

The control unit U is configured to control the eleventh actuator 111 as a function of the measurements of the further sensor 32.

According to an aspect, the immobiliser 10 and each element of the apparatus 1 involved in moving the immobiliser 10 are made in such a way as to not have any cavities or point which can facilitate the collection of organic materials or dirt in general.

Advantageously, this makes these elements of the apparatus 1 easily sterilisable which, in use, may be in direct contact with the patient's breast 15.

It should be noted that the apparatus 1 is configured to be positioned, in use, both horizontally and vertically, that is to say, the machine 2 can have the detection plane S of the X-ray detector 4 both parallel to the horizontal and parallel to the vertical.

According to an aspect of the invention, the control unit U is configured to control one or more between the first actuator 101, second actuator 102, third actuator 103, fourth actuator 104, fifth actuator 105, sixth actuator 106, seventh actuator 107, eighth actuator 108, ninth actuator 109, tenth actuator 110 and eleventh actuator 111.

According to an aspect of this invention, one or more between the first actuator 101, second actuator 102, third actuator 103, fourth actuator 104, fifth actuator 105, sixth actuator 106, seventh actuator 107, eighth actuator 108, ninth actuator 109, tenth actuator 110 and eleventh actuator 111 comprises a motor not illustrated in the accompanying drawings, preferably an electric motor.

The drawings will now be briefly described in relation to the positioning of some parts of the machine 2.

FIG. 1A shows the machine 2 with the probe 50 with the needle 51 perfectly vertical and positioned in the zone 5 above the immobiliser 10 for access to the breast 15 through the opening 14 of the immobilising element 11.

Figure 1B:
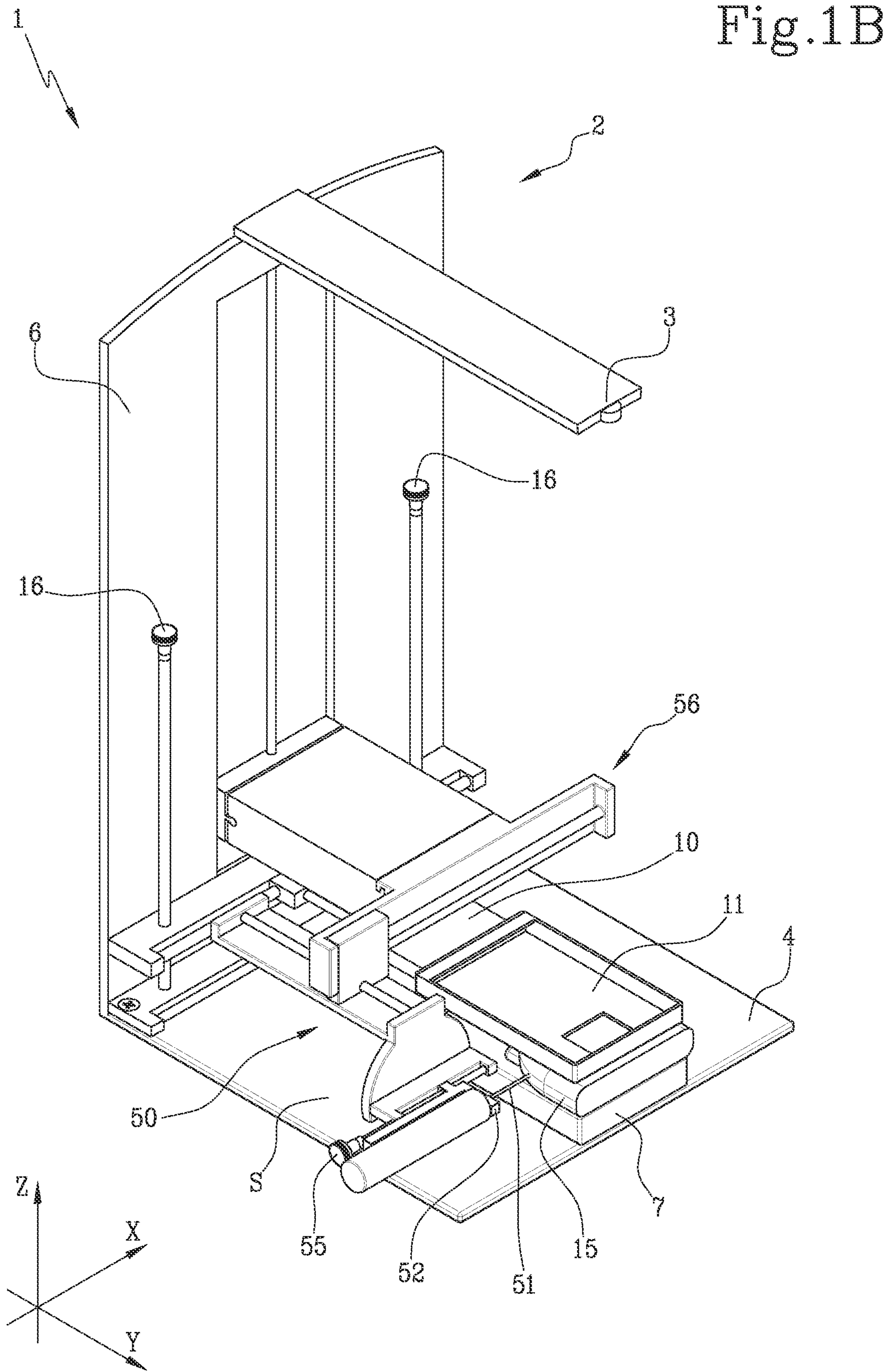
Figure 1C:
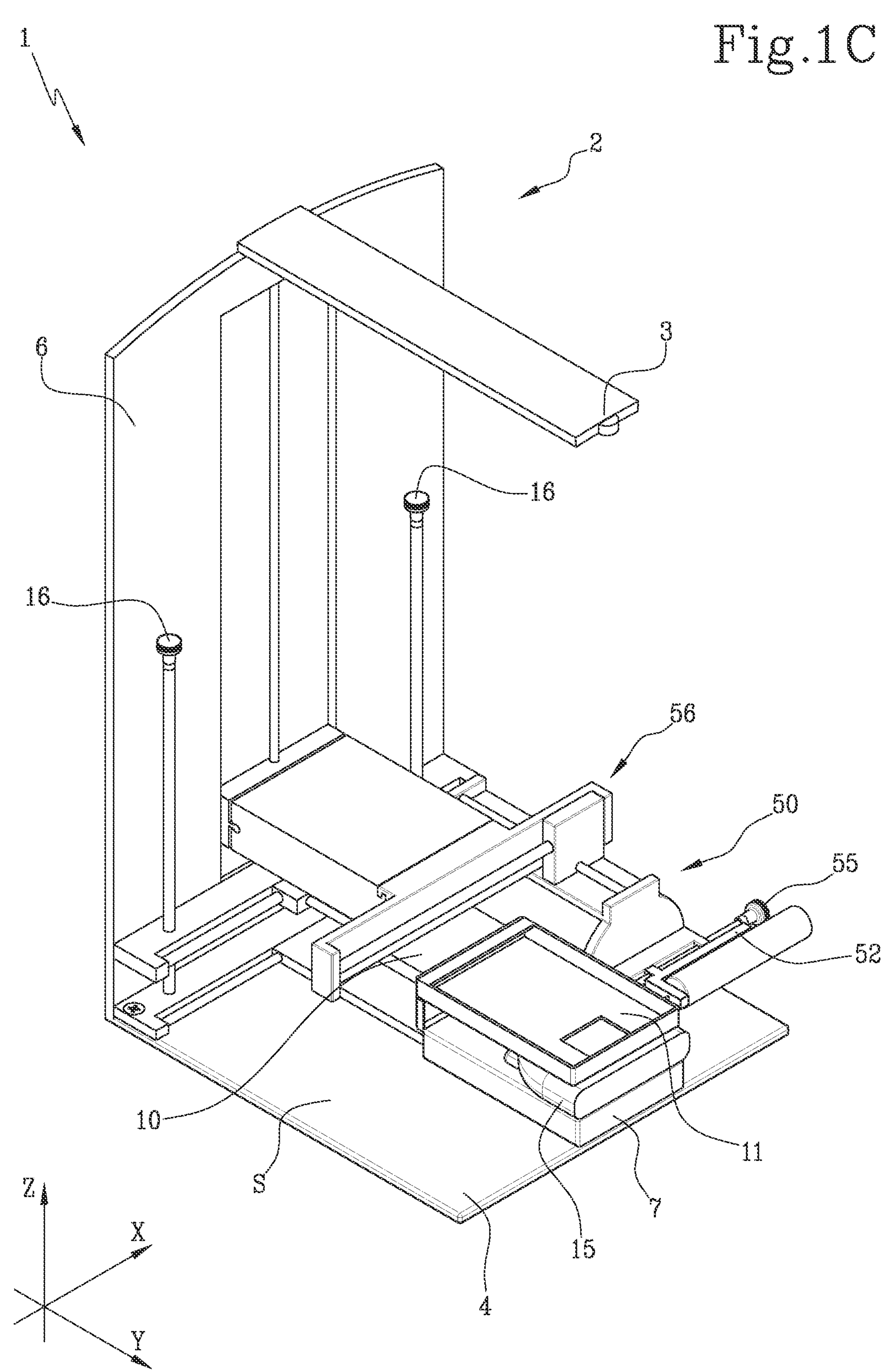

FIGS. 1B and 1C illustrate the machine 2 with the probe 50 with the needle 51 on the left and right sides, respectively, with respect to the immobiliser 10 for a lateral access to the breast 15, with respect to the first direction X.

FIG. 2 shows the machine 2 with the probe 50 with the needle 51 perfectly vertical and positioned in the zone 5 above the immobiliser 10 at the opening 14 of the immobilising element 11.

Figure 3:
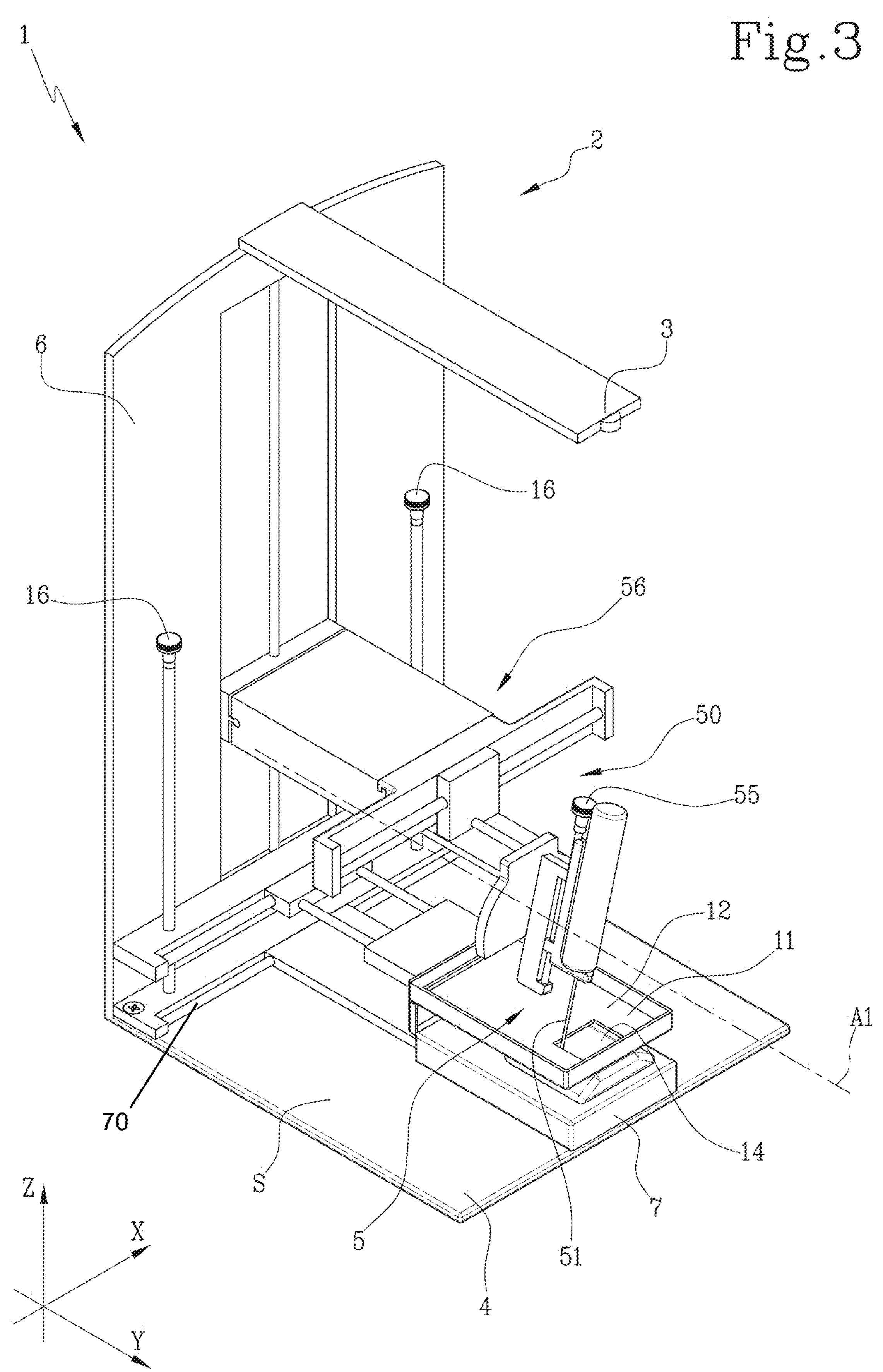

FIG. 3 illustrates the machine 2 with the probe 50 with the needle 51 rotated with respect to the first axis A1 and positioned in the zone 5 above the immobiliser 10 at the opening 14 of the immobilising element 11.

Figure 4:
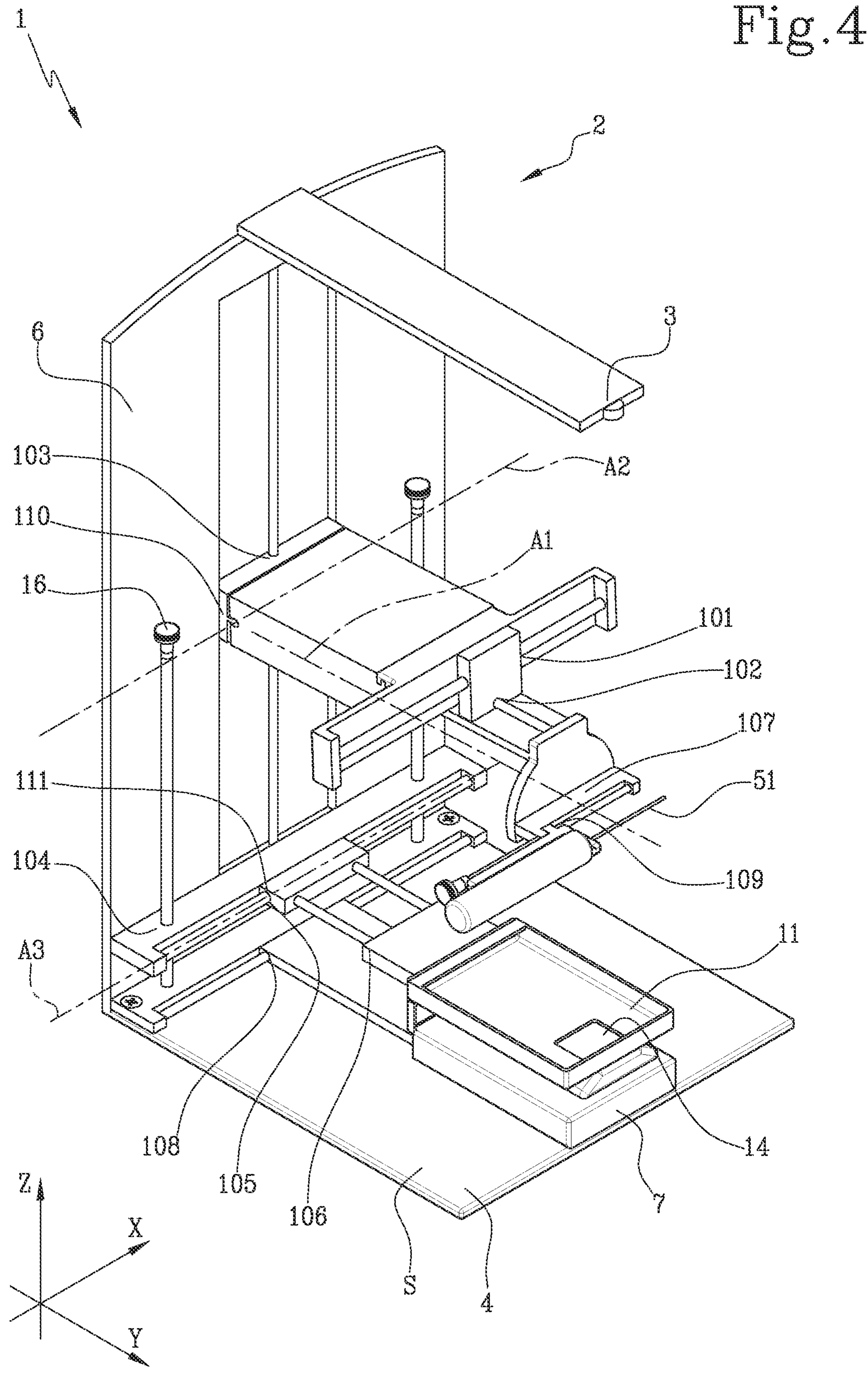
Figure 5:
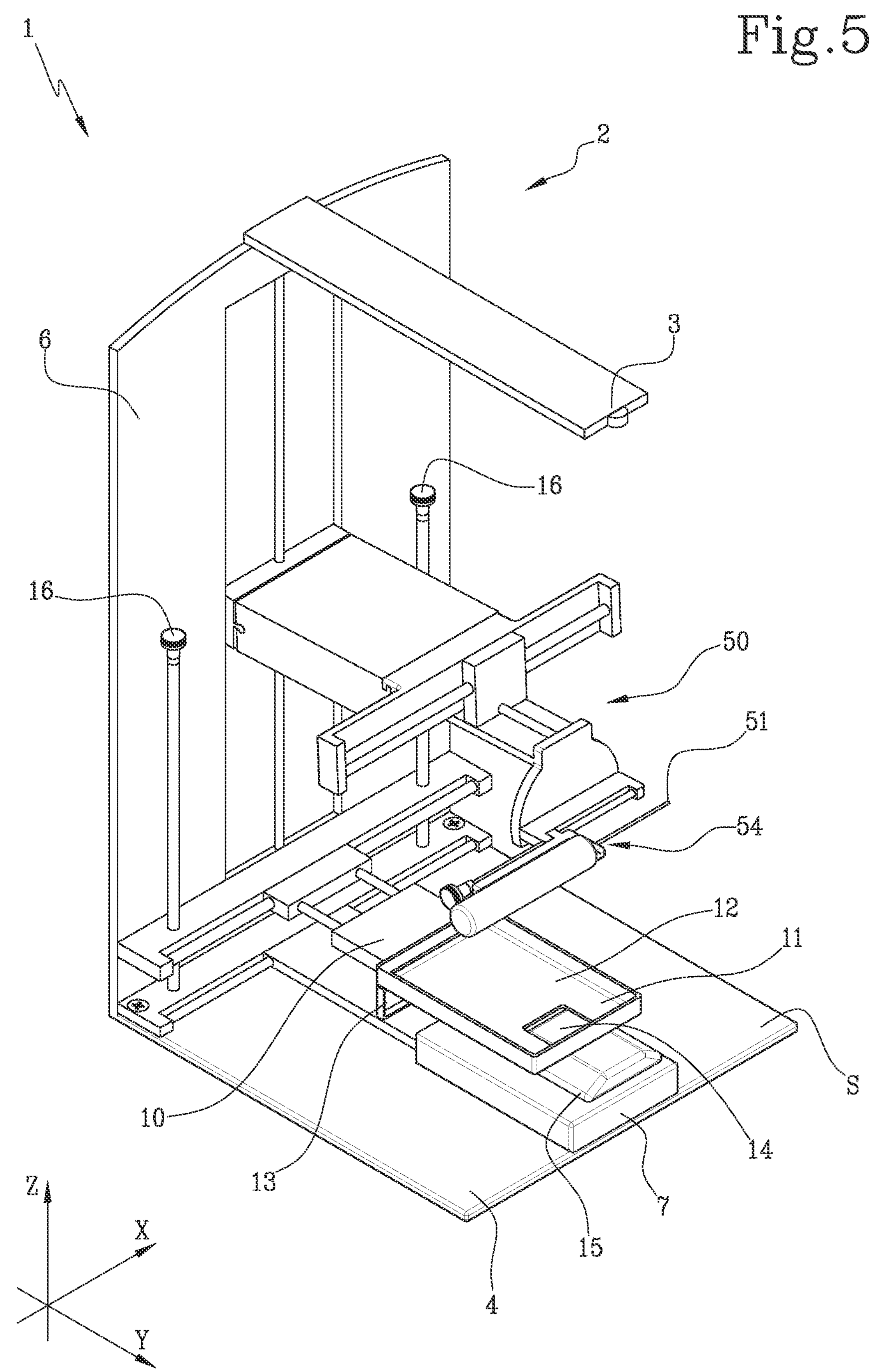

FIGS. 4 and 5 illustrate the machine 2 with the probe 50 with the needle 51 rotated relative to the first axis A1 (by 90°) and with the immobilising element 11 positioned, along the second direction Y, respectively at the front and rear.

Figure 6:
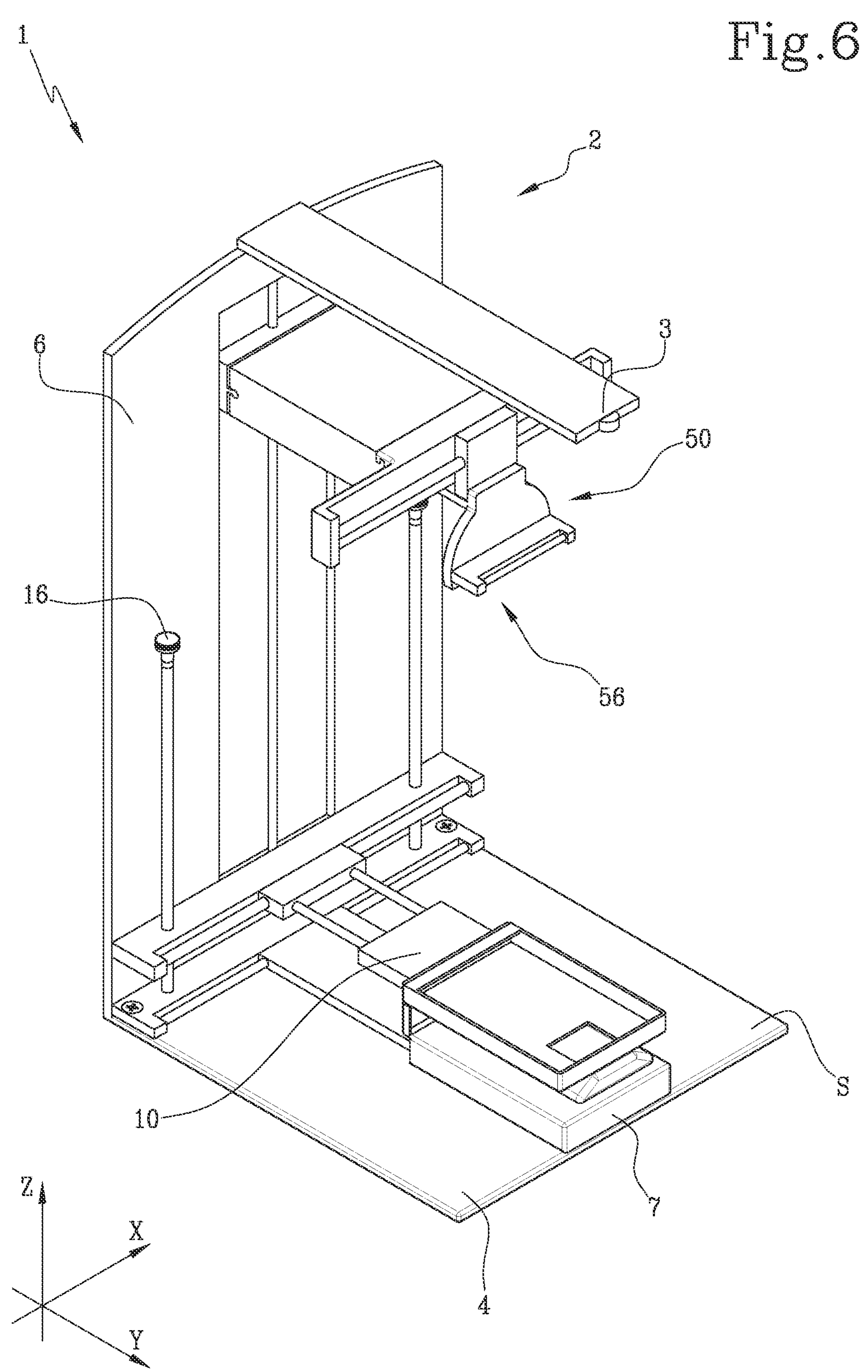

FIG. 6 illustrates the machine 2 with part of the probe 50 removed.

Figure 7:
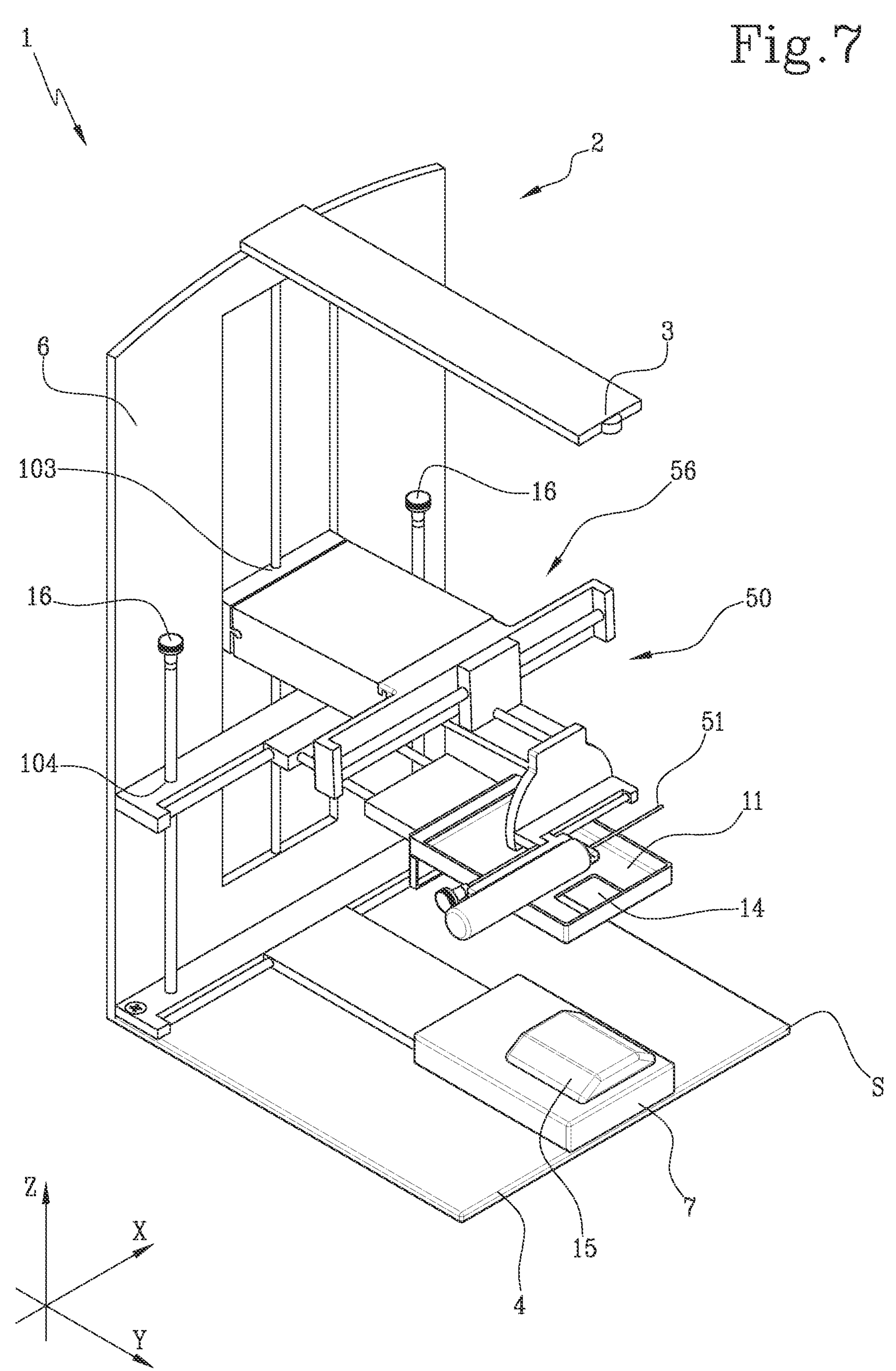

FIG. 7 shows the machine 2 with the immobilising element 11 and the member 7 for supporting the breast 15 in a central position and the probe 50 located above the immobilising element 11; in this drawing, the immobilising element 11 is raised with respect to the member 7 for supporting the breast 15.

Figure 8:
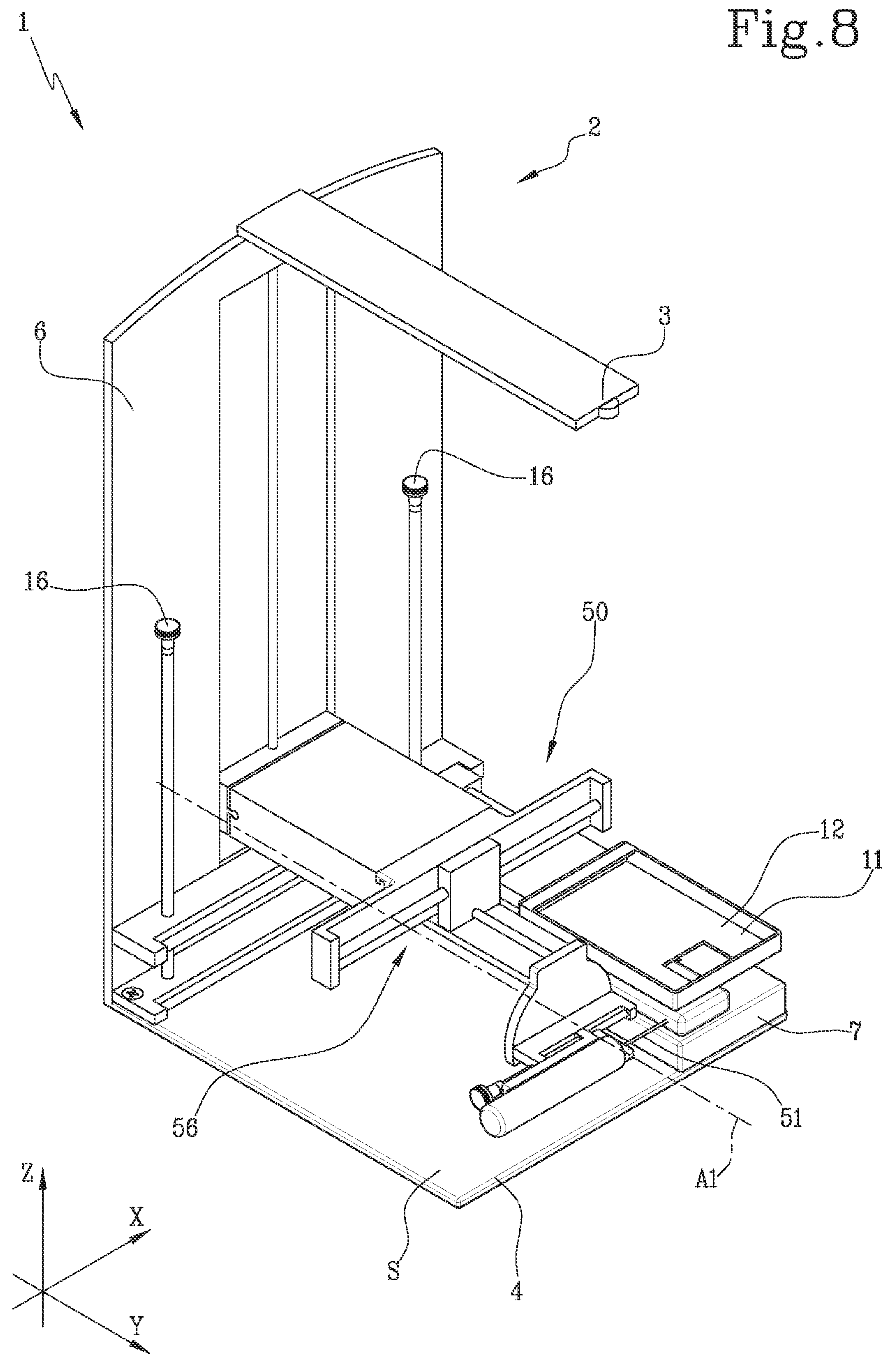

FIG. 8 shows the machine 2 with the immobilising element 11 and the member 7 for supporting the breast 15 in the right-hand position and the probe 50 positioned laterally, on the left, with respect to the immobilising element 11, with respect to the first direction X; a lateral biopsy may be performed in this configuration.

Figure 9:
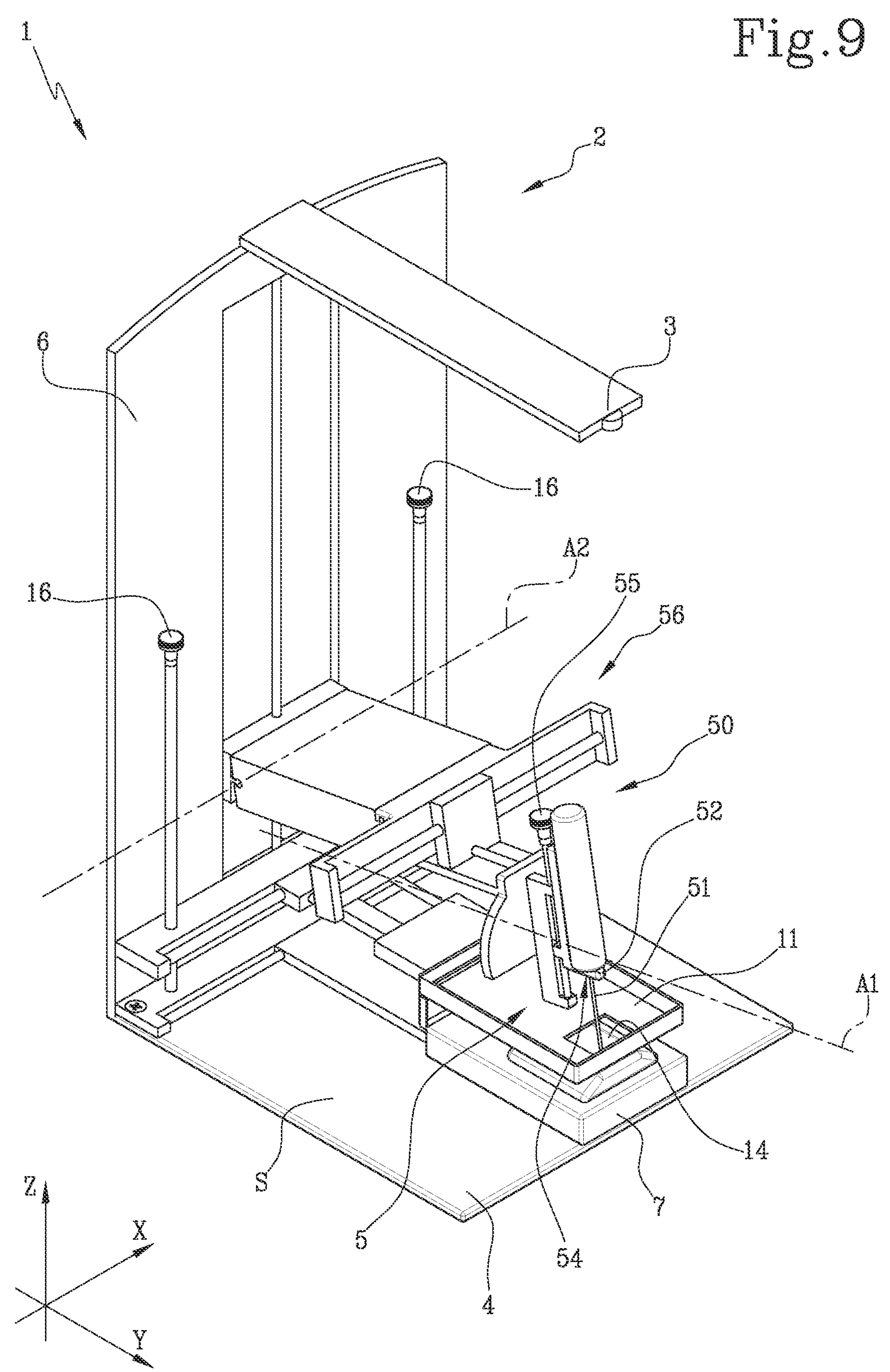

FIG. 9 illustrates the machine 2 with the probe 50 with the needle 51 rotated with respect to the second axis A2 and positioned in the zone 5 above the immobiliser 10 at the opening 14 of the immobilising element 11.

Figure 10:
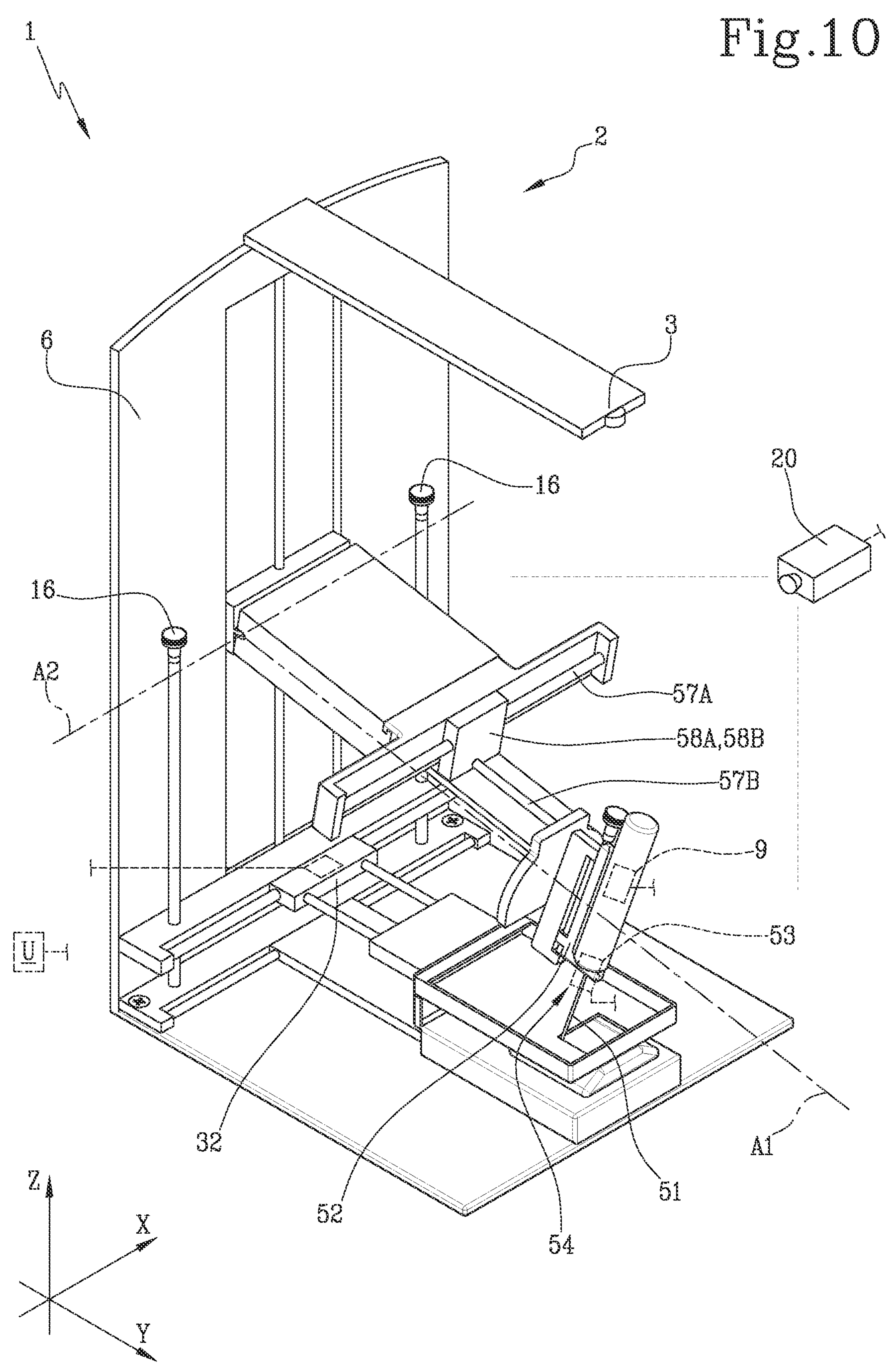

FIG. 10 shows the machine 2 with the probe 50 with the needle 51 rotated with respect to the second axis A2 and also rotated with respect to the first axis A1 and positioned in the zone 5 above the immobiliser 10 at the opening 14 of the immobilising element 11.

Figure 11:
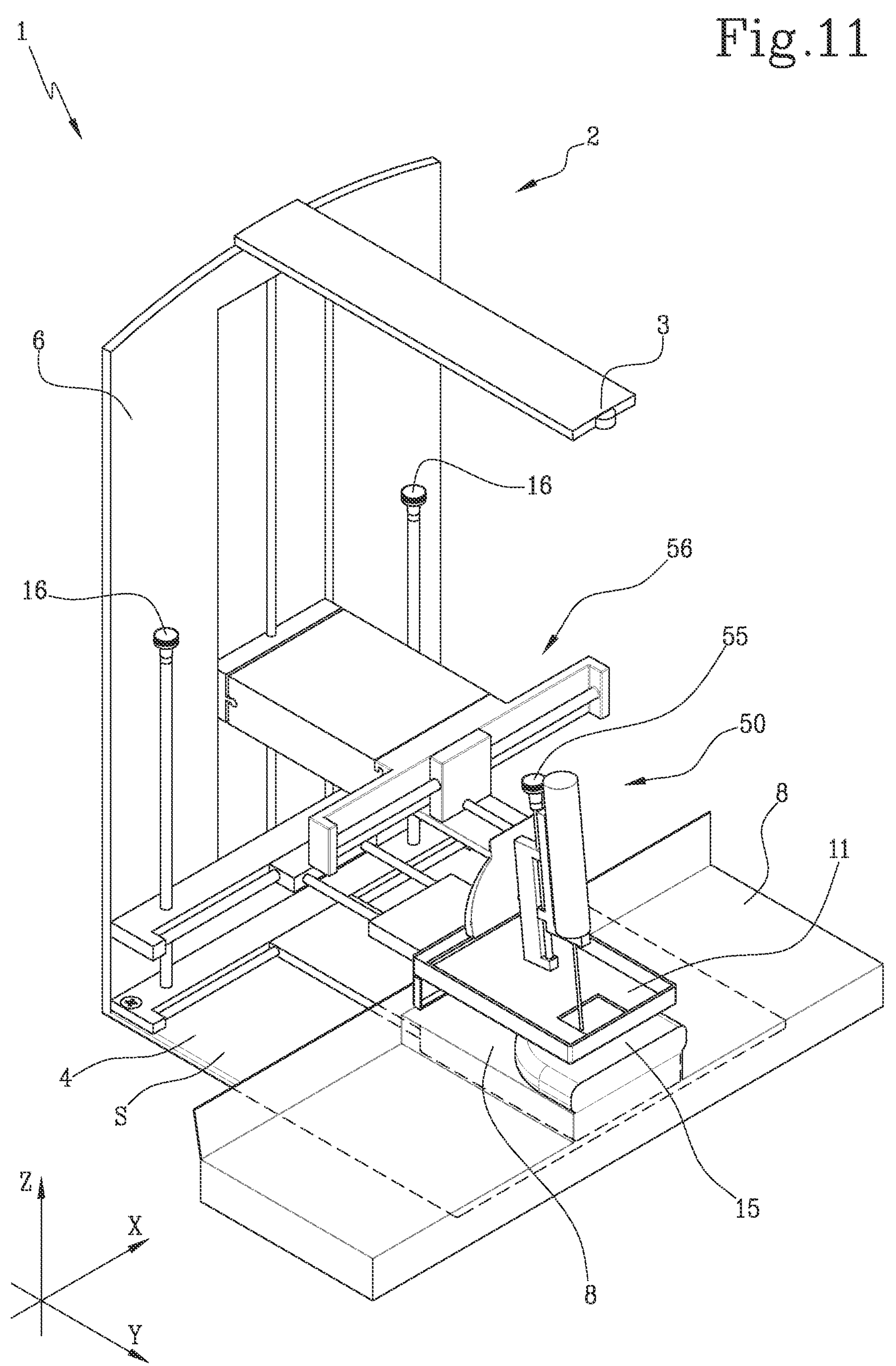

FIG. 11 shows the machine 2 with the probe 50 with the needle 51 positioned in the zone 5 above the immobiliser 10 at the opening 14 of the immobilising element 11 and with the covering system 8 of the detector 4 and/or of the member 7 for supporting the breast 15 coupled to the detector 4 and to the member 7 for supporting the breast 15.

Figure 12:
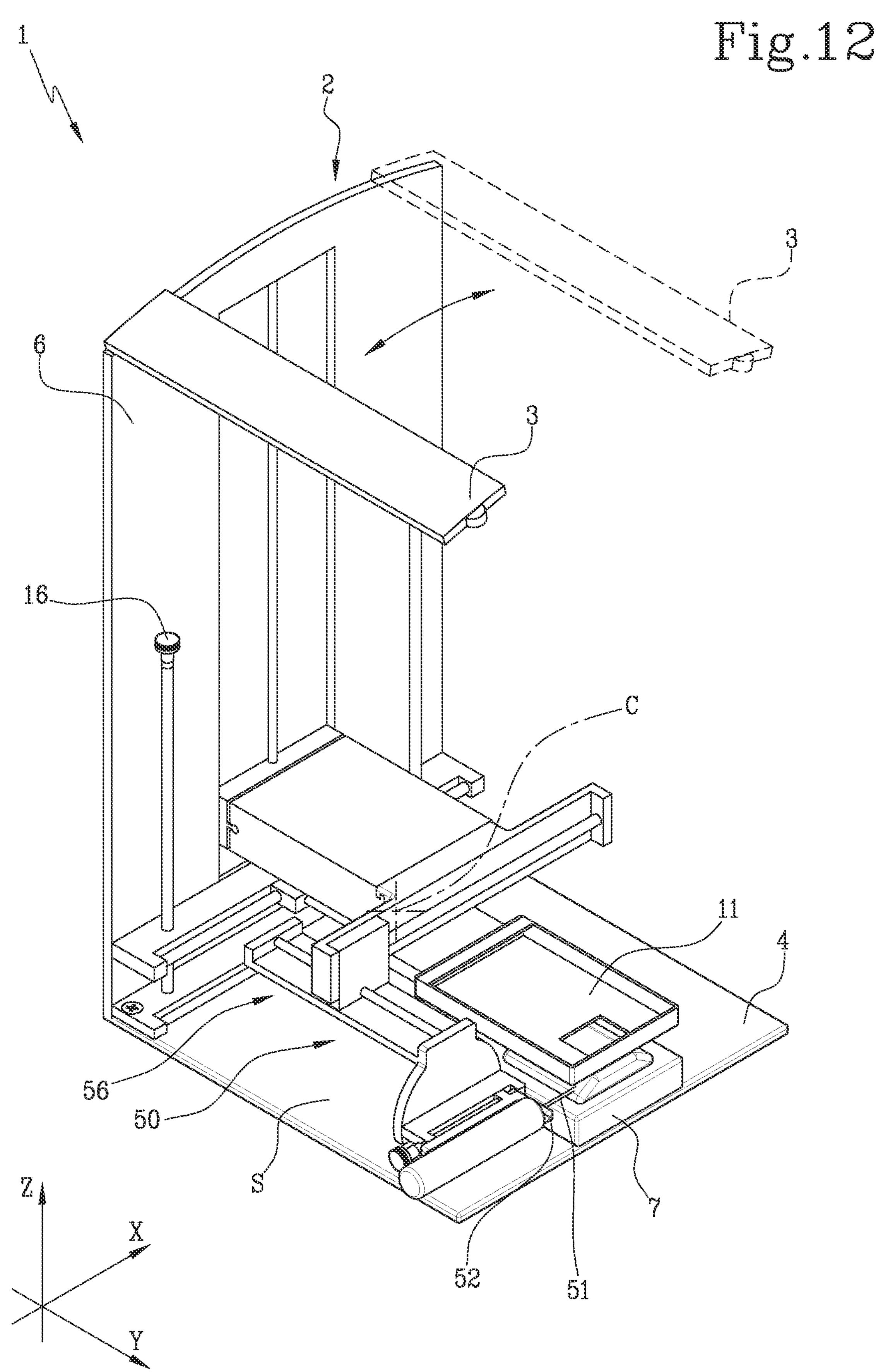

FIG. 12 illustrates the machine 2, highlighting various possible positions which the X-ray source 3 may adopt.

FIGS. 2 to 10 and 12 schematically illustrate, above the supporting member 7, a breast 15.

According to another aspect, a method is also defined, comprising the steps of:

- preparing:
  - at least one source 3 configured to emit X-rays,
  - at least one X-ray detector 4 defining a detection plane S,
  - a probe 50 equipped with a needle 51 for the treatment of the body of a patient,
  - an immobiliser 10 comprising an immobilising element 11,
  - a supporting frame 6, supporting the at least one source 3, the at least one X-ray detector 4, the immobiliser 10 and the probe 50,
  - a control unit U connected at least to the source 3 and to the X-ray detector (4);
- positioning a patient with the relative breast 15 resting on the detection plane S;
- moving the immobilising element 11 along a third direction Z at right angles to the detection plane S, to compress the breast 15 between the immobiliser 10 and the detection plane S;
- moving the probe 50 along a first direction X, along a second direction Y perpendicular to the first direction X and along the third direction Z at a right angle to the detection plane S and moving the probe 50 in the zone 5 above the immobiliser 10 to allow a positioning of the needle 51, along the first direction X, selectively in the zone 5 above the immobiliser 10, on the right or left side relative to the immobiliser 10, wherein said movement of the probe 50 along at least the third direction Z is performed irrespective of the above-mentioned movement of the immobilising element 11 along the third direction Z;
- reconstructing at least one image of the breast 15 by analysing the X-rays emitted by the source 3, passing through the breast 15 and received by the detector 4.

This method is a method for generating an image of the breast 15 of a patient by means of the emission and the detection of X-rays.

According to an aspect, the step of reconstructing at least one image of the breast 15 comprises a first step of reconstructing at least one image of the breast 15 before moving the probe 50 along the first direction X, the second direction Y and the third direction Z.

The step of moving the probe 50 is a function of the at least one image of the breast 15.

According to an aspect, the step of reconstructing at least one image of the breast 15 comprises a second step of reconstructing at least one image of the breast 15 after the step of moving the probe 50 along the first direction X, the second direction Y and the third direction Z.

According to another aspect, the method comprises the step of preparing a member 7 for supporting the breast 15 for resting the breast 15, and positioning said member 7 for supporting the breast 15 between the detection plane S and the immobiliser 10.

According to another aspect, the method comprises the following steps:

- setting the control unit U to activate a mode of identifying a physical characteristic or position of the immobiliser 10, the probe 50 and/or the member 7 for supporting the breast 15 and/or of the breast 15;
- activating the X-ray source 3;
- and analysing the X-ray signal received from the detector 4 to identify the physical characteristic or position of the immobiliser 10, the probe 50, the member 7 for supporting the breast 15 and/or of the breast 15.

According to yet another aspect, the method comprises the following steps:

- preparing a viewing system 20;
- configuring the viewing system 20 to capture images of the immobiliser 10 and/or of the probe 50 and/or of the member 7 for supporting the breast 15 and/or of the breast 15;
- analysing the images of the viewing system 20 to identify a physical characteristic or the position of said immobiliser 10, probe 50, member 7 for supporting the breast 15 or breast 15.

According to an aspect of the invention, the method comprises the steps of:

- moving the X-ray source 3 along an arc in a plurality of different positions for acquiring stereotaxic or tomographic images;
- acquiring stereotaxic or tomographic images of the breast 15 and/or of the immobiliser 10 in said different positions;
- analysing these images to identify a position of the immobiliser 10 and/or of the breast 15 and/or of a lesion in the breast 15;
- moving the probe 50 according to that position of the immobiliser 10 and/or of the breast 15 and/or of a lesion in the breast 15 identified.

According to a further aspect, the method comprises the steps of:

preparing at least one system 8, which is disposable or sterilisable, for covering the detector 4 and/or the member 7 for supporting the breast 15;

removably coupling the covering system 8 to the detector 4 and/or to the member 7 for supporting the breast 15;

carrying out an examination of the breast 15 of a patient;

uncoupling the covering system 8 from the detector 4 and/or from the member 7 for supporting the breast 15 and sterilising the covering system 8.

According to another aspect of the method, the probe 50 is a biopsy probe and the method comprises the steps of:

setting the control unit U to activate a method of targeting the needle 51 during biopsy;

activating the X-ray source 3 in order to capture at least two stereoscopic images;

analysing said stereoscopic images to identify the position of a region of the breast 15 of a patient under examination;

comparing said position identified with a previous stored position of said region of the breast 15 of a patient under examination;

deriving, as a function of said comparison, amplitudes of movement of said needle 51 of the probe 50 and movement of the needle 51, as a function of said amplitudes of movement, to reach with the needle 51 the region of the breast 15 of a patient under examination.

According to another aspect, the method comprises a step of moving the immobilising element 11 along the first direction X and/or the second direction Y.

According to yet another aspect, the method comprises a step of moving the member 7 for supporting the breast 15 along the first direction X and/or the second direction Y.

According to yet another aspect, the method comprises a step of rotating the probe 50, about a first axis of rotation A1, angularly positioned relative to the third direction Z, that is, angularly positioned relative to a direction perpendicular to the detection plane S.

According to yet another aspect, the method comprises a step of rotating the probe 50, about a second axis A2, parallel to the detection plane S and parallel to the first direction X.

According to yet another aspect, the method comprises a step of rotating the immobiliser 10, about a third axis A3, parallel to the detection plane S and parallel to the first direction X.

Advantageously, the method proposed allows an image of the breast 15 to be reconstructed by emitting X-rays in a particularly simple way, simplifying the operations for positioning the breast 15 of the patient during the examination.

The invention claimed is:

1. A medical apparatus for X-ray analysis, comprising:

a machine for allowing a diagnosis, including:

at least one X-ray source configured to emit X-rays, at least one X-ray detector defining a detection plane, a probe including a needle for treatment of a body of a patient, an immobiliser comprising an immobilising element, a supporting frame, supporting the at least one X-ray source, the at least one X-ray detector, the immobiliser and the probe;

a control unit connected at least to the at least one X-ray source and to the at least one X-ray detector;

the probe being connected to the supporting frame movably along a first direction, along a second direction perpendicular to the first direction and along a third direction at right angles to the detection plane, the first direction and the second direction lying in a plane parallel to the detection plane, the apparatus being configured for moving said probe in a zone above the immobiliser to allow a positioning of the needle, along the first direction, selectively in the zone above the immobiliser and on right and left sides of the immobiliser;

the immobiliser being connected to the supporting frame and being movable, independently of the probe, at least along the third direction;

a member for supporting a breast of the patient, the member being removably connected to the supporting frame and positioned between the detection plane and the immobiliser, a support guide aligned along the first direction;

the member for supporting the breast being movable along the support guide along the first direction;

the member for supporting the breast being rigid;

the member for supporting the breast being separate from the at least one X-ray detector so as to be movable along the first direction with respect to the at least one X-ray detector; and the member for supporting the breast being firmly attached to the support guide with respect to the second and third directions to maintain a fixed position to the support guide with respect to the second and third directions.

2. The apparatus according to claim 1, wherein the probe is configured to allow a movement along the first direction for a stroke of between 50 mm and 400 mm.

3. The apparatus according to claim 1, wherein said probe is a biopsy probe.

4. The apparatus according to claim 1, wherein the immobiliser is movable, continuously, independently of the probe, along the first direction.

5. The apparatus according to claim 1, wherein the immobiliser is movable independently of the probe, along the second direction.

6. The apparatus according to claim 1, wherein the probe is movable in rotation about a first axis of rotation.

7. The apparatus according to claim 1, and further comprising a covering system configured for covering the at least one X-ray detector and/or the member for supporting the breast, the covering system being removably couplable to the at least one X-ray detector and/or to the member for supporting the breast, said covering system being disposable or sterilisable.

8. The apparatus according to claim 1, and further comprising at least one sensor connected to the control unit and configured to detect impacts of the probe in a movement of the probe, along the third direction and/or along the first direction and/or the second direction.

9. The apparatus according to claim 1, wherein the probe further comprises a supporting device for the needle, and said apparatus comprises a distance sensor connected to the control unit and configured to measure a distance between a tip of the needle and the supporting device for the needle.

10. The apparatus according to claim 9, wherein the probe further comprises a needle holder guide and the distance sensor is positioned on the needle holder guide.

11. The apparatus according to claim 1, wherein the control unit is configured to provide a mode for identifying a position of the immobiliser and/or a physical characteristic of the breast of the patient, wherein the control unit is configured to activate the at least one X-ray source and identify the position of the immobiliser by analysing a signal received from the at least one X-ray detector.

12. The apparatus according to claim 1, and further comprising a viewing system configured to capture images of at least one of the immobiliser, the probe, the member for supporting the breast, the breast in order to identify a position or physical characteristics of one or more of said immobiliser, probe, member for supporting the breast, breast, relative to a predetermined reference system.

13. The apparatus according to claim 1, wherein the probe further comprises at least one control knob configured to move a supporting device for the needle forwards or backwards relative to a biopsy sampling zone.

14. The apparatus according to claim 1, wherein the probe further comprises a movement system with guides and slides, movable along said guides, for movements along the first direction and the second direction.

15. The apparatus according to claim 14, wherein the movement system with the guides and the slides comprises a first guide and a first slide, movable along said first guide, for the movement along the first direction.

16. The apparatus according to claim 14, wherein the movement system with the guides and the slides comprises a second guide and a second slide, movable along said second guide, for the movement along the second direction.

17. The apparatus according to claim 1, wherein the immobiliser comprises at least a first tray, configured to collect fluids or organic materials.

18. The apparatus according to claim 1, wherein the probe is connected to the supporting frame by a first hinge, to rotate about a second axis parallel to the detection plane.

19. The apparatus according to claim 1, wherein the immobiliser is connected to the supporting frame by a second hinge, to rotate about a third axis parallel to the detection plane.

20. A method comprising the following steps:

providing a machine for allowing a diagnosis, including:

at least one X-ray source configured to emit X-rays, at least one X-ray detector defining a detection plane, a probe, including a needle, for treatment of a body of a patient, an immobiliser comprising an immobilising element, a supporting frame, supporting the at least one X-ray source, the at least one X-ray detector, the immobiliser and the probe, a control unit connected at least to the at least one X-ray source and to the at least one X-ray detector;

the probe being connected to the supporting frame movably along a first direction, along a second direction perpendicular to the first direction and along a third direction at right angles to the detection plane, the first direction and the second direction lying in a plane parallel to the detection plane, the machine being configured for moving said probe in a zone above the immobiliser to allow a positioning of the needle, along the first direction, selectively in the zone above the immobiliser and on right and left sides of the immobiliser;

the immobiliser being connected to the supporting frame and being movable, independently of the probe, at least along the third direction;

a member for supporting a breast of the patient, the member being removably connected to the supporting frame and positioned between the detection plane and the immobiliser, a support guide aligned along the first direction;

the member for supporting the breast being movable along the support guide along the first direction;

the member for supporting the breast being rigid;

the member for supporting the breast being separate from the at least one X-ray detector so as to be movable along the first direction with respect to the at least one X-ray detector; and the member for supporting the breast being firmly attached to the support guide with respect to the second and third directions to maintain a fixed position to the support guide with respect to the second and third directions;

positioning the patient with the breast resting on the detection plane;

moving the immobilising element along a third direction at right angles to the detection plane, to compress the breast between the immobiliser and the detection plane, moving the probe along the first direction, along the second direction and along the third direction and moving the probe in the zone above the immobiliser to allow the positioning of the needle, along the first direction, selectively in the zone above the immobilizer and on right and left sides of the immobiliser, wherein said movement of the probe along at least the third direction is performed irrespective of the movement of the immobilising element along the third direction;

reconstructing at least one image of the breast by analysing the X-rays emitted by the at least one X-ray source, passing through the breast and received by the at least one X-ray detector.

21. The method according to claim 20, and further comprising preparing the member for supporting the breast for resting the breast, and positioning said member for supporting the breast between the detection plane and the immobiliser.

22. The method according to claim 21, and further comprising:

setting the control unit to activate a mode of identifying a physical characteristic or a position of the immobiliser, the probe and/or the member for supporting the breast and/or of the breast;

activating the at least one X-ray source; and analysing an X-ray signal received from the at least one X-ray detector to identify the physical characteristic or the position of the immobiliser, the probe, the member for supporting the breast and/or of the breast.

23. The method according to claim 21, and further comprising:

preparing a viewing system;

configuring the viewing system to capture images of the immobiliser and/or of the probe and/or of the member for supporting the breast and/or of the breast;

analysing the images of the viewing system to identify a physical characteristic or a position of said immobiliser, probe, member for supporting the breast or breast.

24. The method according to claim 21, and further comprising:

preparing at least one covering system for covering the at least one X-ray detector and/or the member for supporting the breast, said at least one covering system being disposable or sterilisable;

removably coupling the at least one covering system to the at least one X-ray detector and/or to the member for supporting the breast;

carrying out an examination of the breast of a patient;

uncoupling the at least one covering system from the at least one X-ray detector and/or from the member for supporting the breast and sterilising the at least one covering system.

25. The method according to claim 20, wherein said probe is a biopsy probe, and further comprising:

setting the control unit to activate a method of targeting the needle during biopsy;

activating the at least one X-ray source in order to capture at least two stereoscopic images;

analysing said at least two stereoscopic images to identify a position of a region of the breast of the patient under examination;

comparing said position identified with a previously stored position of said region of the breast of the patient under examination;

deriving, as a function of said comparison, movement of said needle to reach with the needle the region of the breast of the patient under examination.

* * * * *